United States Patent [19]

Macholdt et al.

[11] Patent Number: 5,329,046
[45] Date of Patent: Jul. 12, 1994

[54] BISCATIONIC ACID AMIDE AND IMIDE DERIVATIVES AND PROCESSES FOR THEIR PREPARATION

[75] Inventors: Hans-Tobias Macholdt, Darmstadt; Siegfried Schiessler, Bad Soden am Taunus; Jörg Gitzel, Hattersheim am Main; Erwin Dietz, Kelkheim/Taunus, all of Fed. Rep. of Germany

[73] Assignee: Hoechst Aktiengesellschaft, Frankfurt am Main, Fed. Rep. of Germany

[21] Appl. No.: 867,185

[22] PCT Filed: Dec. 17, 1990

[86] PCT No.: PCT/EP90/02199

§ 371 Date: Jun. 25, 1992

§ 102(e) Date: Jun. 25, 1992

[87] PCT Pub. No.: WO91/09835

PCT Pub. Date: Jul. 11, 1991

[30] Foreign Application Priority Data

Dec. 28, 1989 [DE] Fed. Rep. of Germany ....... 3943047
Sep. 5, 1990 [DE] Fed. Rep. of Germany ....... 4028121

[51] Int. Cl.⁵ .................................................. C07F 5/02
[52] U.S. Cl. ......................................... 564/8; 540/452; 544/69; 544/229; 546/13; 548/110; 548/405; 556/47; 562/564
[58] Field of Search ................................... 564/8, 156

[56] References Cited

U.S. PATENT DOCUMENTS 4,299,982  11/1981  Redmore et al. .................. 564/156

FOREIGN PATENT DOCUMENTS 0026157  4/1981  European Pat. Off. .
0122324  10/1984  European Pat. Off. .
0125475  11/1984  European Pat. Off. .
0327379  8/1989  European Pat. Off. .
2056699  3/1981  United Kingdom .
2112388  7/1983  United Kingdom .

Primary Examiner—Shailendra Kumar

[57] ABSTRACT

The invention relates to biscationic acid amide and acid imide derivatives with an anion of formula $(BR_9R_{10}R_{11}R_{12})^-$, where $R_9$ to $R_{12}$ are aliphatic, iso- or heterocyclic aromatic residues or aralkyl residues, which may be substituted by $C_1$-$C_4$-alkyl residues, $C_1$-$C_4$-alkoxy residues, aryl residues or halogen atoms (e.g. fluorine atoms), and mixtures of these compounds and mixed crystals with mixed anions and/or cations. The invention also relates to a process for preparing them. The new compounds are excellent colorless charge controllers in toners and developers for electrophotographic recording and as charge-enhancers in powders and paints for surface coating, in particular in triboelectrically or electrokinetically sprayed powder paints.

6 Claims, No Drawings

BISCATIONIC ACID AMIDE AND IMIDE DERIVATIVES AND PROCESSES FOR THEIR PREPARATION

The present invention relates to novel biscationic acid amide and imdie derivatives and processes for their preparation. The present invention specifically relates to novel biscationic acid amide and imide derivatives of the general formulae (I) to (III):

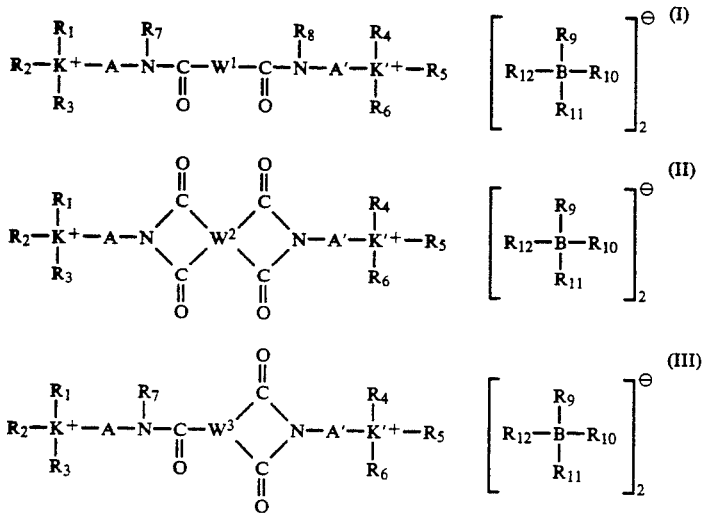

in which $R_2$ to $R_8$ independently of one another are in each case a hydrogen atom or a radical based on a hydrocarbon, such as, for example, a straight-chain or branched, saturated or unsaturated alkyl group having 1 to 30 carbon atoms, preferably having 1 to 22 carbon atoms, a polyoxalkylene group of the general formula -[alkylene($C_1$-$C_5$)—O]$_n$—R, in which R is a hydrogen atom, an alkyl($C_1$-$C_4$) group or an acyl group, such as, for example, an acetyl, benzoyl or naphthoyl group, and n is a number from 1 to 10, preferably from 1 to 4, a mono- or polynuclear cycloaliphatic radical having 5 to 12 carbon atoms, such as, for example, a cyclopentyl or cyclohexyl radical, a mono- or polynuclear aromatic radical, such as, for example, a phenyl, naphthyl, tolyl or biphenyl radical, or an araliphatic radical, such as, for example, a benzyl radical, in which the aliphatic, cycloaliphatic, araliphatic or aromatic radicals mentioned can be substituted by carboxylic or sulfonic acid groups, salts or amides or esters thereof, alkyl ($C_1$-$C_4$), hydroxyl or alkoxy ($C_1$-$C_4$) groups, primary, secondary or tertiary amino groups, such as, for example, N-monoalkyl ($C_1$-$C_4$) amino or N-dialkyl ($C_1$-$C_4$)amino groups, and by fluorine, chlorine or bromine atoms, the aliphatic radicals preferably by 1 to 45 fluorine atoms, and the aliphatic radicals mentioned and the cycloaliphatic, araliphatic or aromatic ring systems can contain one or more hetero atoms, such as, for example, nitrogen and/or oxygen and/or sulfur and/or phosphorus atoms, and $R_1$ and $R_2$, or $R_4$ and $R_5$ independently of one another, incorporating K or K' can be closed together to form a saturated or unsaturated, preferably aromatic, 5- to 7-membered ring system, which can contain further hetero atoms, preferably nitrogen and/or oxygen and/or sulfur atoms, and can be substituted and/or modified by condensing with or bridging to further ring systems, and in which, in the case where $R_1$ or $R_2$, or $R_4$ or $R_5$ in this connection forms a double bond to K or K', $R_3$ and $R_6$ have no subject, and/or one of the radicals $R_1$, $R_2$ or $R_3$ can be closed together with $R_7$ or one of the radicals $R_4$, $R_5$ or $R_6$ can be closed together with $R_6$ to form an aliphatic bridge of 2 to 5 carbon atoms, and A and A' independently of one another are in each case a bridge member based on a hydrocarbon radical, such as, for example, a straight-chain or branched, saturated or unsaturated alkylene bridge member having 1 to 30 carbon atoms, preferably having 1 to 12 carbon atoms, a mono- or polynuclear cycloaliphatic bridge member, such as, for example, a cyclopentylene or cyclohexylene member, a mono- or polynuclear aromatic bridge member, such as, for example, a phenylene, naphthylene, tolylene or biphenylene member, or an araliphatic bridge member, such as, for example, a benzylene, xylylene, mesitylene or benzoyleneamide member, in which the aliphatic, cycloaliphatic, araliphatic or aromatic bridge members can be substituted by carboxylic or sulfonic acid groups, salts or amides or esters thereof, alkyl($C_1$-$C_4$), hydroxyl or alkoxy ($C_1$-$C_4$) groups, primary, secondary or tertiary amino groups, such as, for example, N-monoalkyl ($C_1$-$C_4$)-amino or N-dialkyl(-$C_1$-$C_4$)amino groups, and by fluorine, chlorine or bromine atoms, the aliphatic radicals preferably by 1 to 45 fluorine atoms, and the aliphatic, cycloaliphatic, araliphatic or aromatic bridge members mentioned can contain one or more hetero atoms, such as, for example, nitrogen and/or oxygen and/or sulfur and/or phosphorus atoms, and $W^1$ as a divalent bridge member is a straight-chain or branched, saturated or unsaturated aliphatic bridge member having 1 to 30 carbon atoms, preferably having 1 to 22 carbon atoms, a polyoxyalkylene member, preferably a polyoxyethylene or polyoxypropylene member, of the general formula —$CH_2$—[alkylene($C_1$-$C_5$)—O]$_m$—$CH_2$—, in which m is a number from 0 to 10, preferably from 1 to 4, a mono- or polynuclear cycloaliphatic bridge member having 5 to 12 carbon atoms, such as, for example, a cyclopentylene or cyclohexylene member, a mono- or polynuclear aromatic bridge member, such as, for example, a phenylene, naphthylene, tolylene or biphenylene member, or an araliphatic bridge member, such as, for example, a benzylene member, in which the aliphatic, cycloaliphatic, araliphatic and aromatic bridge members can be substituted by carboxylic or sulfonic acid groups, salts or amides or esters thereof, alkyl($C_1$-$C_4$), hydroxyl or alkoxy($C_1$-$C_4$) groups, primary, secondary or tertiary amino groups, such as, for example, N-monoalkyl(-$C_1$-$C_4$)amino or N-dialkyl($C_1$-$C_4$)amino groups, and by fluorine, chlorine or bromine atoms, the aliphatic radicals preferably by 1 to 45 fluorine atoms, and the aliphatic, cycloaliphatic, araliphatic or aromatic bridge members mentioned can contain one or more hetero atoms, such as, for example, nitrogen and/or oxygen and/or sulfur and/or phosphorus atoms, but $W^1$ can also be a direct bond, and $W^2$ as a tetravalent bridge member is a straight-chain or branched, saturated or unsaturated aliphatic bridge member having 2 to 30 carbon atoms, preferably 2 to 12 carbon atoms, a mono- or polynuclear cycloaliphatic bridge member having 5 to 12 carbon atoms, such as, for example, a cyclopentylene or cyclohexylene member, a mono- or polynuclear aromatic bridge member, such as, for example, a phenylene, naphthylene, tolylene or biphenylene member, or an araliphatic bridge member, such as, for example, a benzylene member, in which the aliphatic, cycloaliphatic, araliphatic and aromatic bridge members can be substituted by carboxylic or sulfonic acid groups, salts or amides or esters thereof, alkyl($C_1$-$C_4$), hydroxyl or alkoxy($C_1$-$C_4$) groups, primary, secondary or tertiary amino groups, such as, for example, N-monoalkyl($C_1$-$C_4$)amino or N-dialkyl($C_1$-$C_4$)amino groups, and by fluorine, chlorine or bromine atoms, the aliphatic radicals preferably by 1 to 45 fluorine atoms, and the aliphatic, cycloaliphatic, araliphatic or aromatic bridge members mentioned can contain one or more hetero atoms, such as, for example, nitrogen and/or oxygen and/or sulfur and/or phosphorus atoms, and $W^3$ as a trivalent bridge member is a straight-chain or branched, saturated or unsaturated aliphatic bridge member having 2 to 30 carbon atoms, preferably 2 to 12 carbon atoms, a mono- or polynuclear cycloaliphatic bridge member having 5 to 12 carbon atoms, such as, for example, a cyclopentylene or cyclohexylene member, a mono- or polynuclear aromatic bridge member, such as, for example, a phenylene, naphthylene, tolylene or biphenylene member, or an araliphatic bridge member, such as, for example, a benzylene member, in which the aliphatic, cycloaliphatic, araliphatic and aromatic bridge members can be substituted by carboxylic or sulfonic acid groups, salts or amides or esters thereof, alkyl($C_1$-$C_4$), hydroxyl or alkoxy($C_1$-$C_4$) groups, primary, secondary or tertiary amino groups, such as, for example, N-monoalkyl($C_1$-$C_4$)-amino or N-dialkyl($C_1$-$C_4$)amino groups, and by fluorine, chlorine or bromine atoms, the aliphatic radicals preferably by 1 to 45 fluorine atoms, and the aliphatic, cycloaliphatic, araliphatic or aromatic bridge members mentioned can contain one or more hetero atoms, such as, for example, nitrogen and/or oxygen and/or sulfur and/or phosphorus atoms, and K and K' independently of one another are a nitrogen, phosphorus, arsenic or antimony atom, preferably a nitrogen atom, and the radicals $R_9$ to $R_2$ independently of one another are aliphatic radicals, such as, for example, methyl, ethyl, propyl, decyl or stearyl radicals, cycloaliphatic radicals, such as, for example, cyclopentyl or cyclohexyl radicals, iso- or heterocyclic aromatic radicals, such as, for example, phenyl, tolyl, naphthyl or pyridyl radicals, or aralkyl radicals, such as, for example, benzyl radicals, in which the aliphatic, cycloaliphatic, araliphatic and aromatic radicals mentioned can be substituted by alkyl($C_1$-$C_4$), alkoxy($C_1$-$C_4$) or aryl radicals or halogen atoms, or are fluorine atoms, and to mixtures of these compounds and mixed crystals with mixed anions and/or cations.

The invention particularly relates to those compounds of the abovementioned general formulae (I) to (III) in which $R_1$ to $R_6$ independently of one another are in each case a hydrogen atom or a straight-chain or branched alkyl($C_1$-$C_6$) group, such as, for example, a methyl, ethyl, n-propyl, iso-propyl, tertiary butyl, pentyl or hexyl group, and those in which $R_1$ and $R_2$, or $R_4$ and $R_5$ independently of one another, incorporating K or K', in which K and K' are nitrogen atoms, can be closed together to form a saturated or unsaturated heterocyclic ring system having one or more nitrogen atom(s) as the hetero atom, such as, for example, pyrrole, pyrroline, pyrrolidine, pyrazole, pyrazolone, pyrazoline, imidazole, oxazole, thiazole, triazole, pyridine, piperidine, pyrazine, piperazine, pyrimidine, hexamethyleneimine or morpholine, in which these ring systems can in turn be substituted, preferably by straight-chain alkyl($C_1$-$C_4$) groups, and/or can be enlarged by condensing with or bridging to further ring systems, such as, for example, to quinoline, indole, indoline, purine, quinoxaline, benzothiazole, acridine, benzoquinoline, carbazole, benzophenazine, phenanthroline, bipiperidine, bipyridine, phenazine, benzacridine or nicotine, in which $R_3$ and/or $R_6$ are in each case a hydrogen atom or an alkyl($C_1$-$C_4$) group, and in the case where $R_1$ or $R_2$, or $R_4$ or $R_5$ forms a double bond to K or K', $R_3$ and $R_6$ have no subject, $R_7$ and $R_8$ are a hydrogen atom, A and A' independently of one another are a —CH$\alpha$C(COOH)—CH$_2$—, —CH$_2$—(CH$_2$—CH=CH—)$_n$— or —(CH$_2$—)$_n$— bridge member where n is 1 to 12, preferably where n is 1 to 4, or a phenylene, naphthylene or — —CO—NH—(CH$_2$)$_3$— bridge member, $W^1$ is a phenylene, naphthylene, cyclohexylene or —(CH$_2$—)$_q$— bridge member, where q is 1 to 12, or a —CH$_2$—O—(CH$_2$-CH$_2$—O)$_r$—CH$_2$— bridge member, where r is 1 to 4, $W^2$ is an ethylenediaminetetramethylene, phenylene or naphthylene bridge member, in which the carboxyl groups required for imide bonding are in each case in the ortho-position relative to one another in the case of the phenylene member and in the ortho- and/or peri-position relative to one another in the case of the naphthylene member, and $W^3$ is a phenylene or naphthylene bridge member, in which at least two carboxyl groups which participate in the imide bond are in the ortho- or peri-position relative to one another and the third carboxyl group can be in any desired position relative to this, and for A and A' and $W^1$ are bridged to the particular K or K' on the one side and imide or amide nitrogen on the other side or substituted by the particular carbonyl functions in the 1,2-, 1,3- or 1,4-position, preferably in the 1,3-or 1,4-position, as phenylene bridge members, in the 1,2-to 1,8- or in the 2,3- to 2,8-position as naphthylene bridge members and the cyclohexylene bridge members in the 1,2-, 1,3- or 1,4-position, preferably in the 1,3- or 1,4-position, and the radicals $R_9$ to $R_{12}$ are phenyl, naphthyl, fluorophenyl, chlorophenyl, methoxyphenyl, biphenyl, pyridyl or tolyl radicals or fluorine atoms, and to mixtures of these compounds and mixed crystals with mixed anions and/or cations.

The following may be mentioned as examples of individual compounds of the abovementioned general formulae (I) to (III):

| Compound | Cation | Anion |
|---|---|---|
| 1.1a | $H_3C-\overset{CH_3}{\underset{CH_3}{N^+}}-(H_2C)_3\overset{H}{N}-\overset{O}{\overset{\|}{C}}-\bigcirc-\overset{O}{\overset{\|}{C}}-\overset{H}{N}(CH_2)_3-\overset{CH_3}{\underset{CH_3}{N^+}}-CH_3$ | $2BF_4^-$ |
| 1.1b | see above | $2B(\text{C}_6H_5)_4^-$ |
| 1.1c | see above | $2B(\text{C}_6H_4\text{-}CH_3)_4^-$ |
| 1.1d | see above | $2B(\text{C}_6H_4\text{-}Cl)_4^-$ |
| 1.1e | see above | $2B(\text{naphthyl})_4^-$ |
| 1.2a | $H-\overset{CH_3}{\underset{CH_3}{{}^+N}}-(H_2C)_3\overset{H}{N}-\overset{O}{\overset{\|}{C}}-\bigcirc-\overset{O}{\overset{\|}{C}}-\overset{H}{N}(CH_2)_3\overset{CH_3}{\underset{CH_3}{N^+}}-H$ | $2BF_4^-$ |
| 1.2b | see above | $2B(\text{C}_6H_5)_4^-$ |
| 1.2c | see above | $2B(\text{C}_6H_4\text{-}CH_3)_4^-$ |
| 1.2d | see above | $2B(\text{C}_6H_4\text{-}Cl)_4^-$ |
| 1.2e | see above | $2B(\text{naphthyl})_4^-$ |

| Compound | Cation | Anion |
|---|---|---|
| 1.3a | H₅C₂—⁺N(CH₃)(C₂H₅)(H₂C)₃NH—CO—C₆H₄—CO—NH(CH₂)₃N⁺(CH₃)(C₂H₅)—C₂H₅ | 2BF₄⁻ |
| 1.3b | see above | 2B(C₆H₅)₄⁻ |
| 1.4a | H₃C—⁺N(CH₃)₂(H₂C)₂NH—CO—C₆H₄—CO—NH(CH₂)₂N⁺(CH₃)₂—CH₃ | 2BF₄⁻ |
| 1.4b | see above | 2B(C₆H₅)₄⁻ |
| 1.5a | H₃C—⁺N(CH₃)₂(H₂C)₁₀NH—CO—C₆H₄—CO—NH(CH₂)₁₀N⁺(CH₃)₂—CH₃ | 2BF₄⁻ |
| 1.5b | see above | 2B(C₆H₅)₄⁻ |
| 1.6a | (N-methylimidazolium)-(CH₂)₃NH—CO—C₆H₄—CO—NH(CH₂)₃-(N-methylimidazolium) | 2BF₄⁻ |
| 1.6b | see above | 2B(C₆H₅)₄⁻ |
| 1.7a | (N-methylpiperidinium)-(CH₂)₃NH—CO—C₆H₄—CO—NH(CH₂)₃-(N-methylpiperidinium) | 2BF₄⁻ |
| 1.7b | see above | 2B(C₆H₅)₄⁻ |
| 1.8a | (N-methylmorpholinium)-(CH₂)₃NH—CO—C₆H₄—CO—NH(CH₂)₃-(N-methylmorpholinium) | 2BF₄⁻ |
| 1.8b | see above | 2B(C₆H₅)₄⁻ |

-continued

| Compound | Cation | Anion |
|---|---|---|
| 1.9a | H₅C₂—N⁺(CH₃)(CH₃)(H₂C)₂N(H)—C(O)—C₆H₄—C(O)—N(H)(CH₂)₃N⁺(CH₃)(CH₃)—C₂H₅ | 2BF₄⁻ |
| 1.9b | see above | 2B(C₆H₅)₄⁻ |
| 1.10a | H₅C₂—N⁺(C₂H₅)(C₂H₅)(CH₂)₃N(H)—C(O)—C₆H₄—C(O)—N(H)(CH₂)₃N⁺(C₂H₅)(C₂H₅)—C₂H₅ | 2BF₄⁻ |
| 1.10b | see above | 2B(C₆H₅)₄⁻ |
| 1.11a | H—⁺N(C₂H₅)(C₂H₅)(H₂C)₃N(H)—C(O)—C₆H₄—C(O)—N(H)(CH₂)₃N⁺(C₂H₅)(C₂H₅)—H | 2BF₄⁻ |
| 1.11b | see above | 2B(C₆H₅)₄⁻ |
| 1.11c | see above | 2B(C₆H₄CH₃)₄⁻ |
| 1.11d | see above | 2B(C₆H₄Cl)₄⁻ |
| 1.11e | see above | 2B(naphthyl)₄⁻ |
| 2.1a | meta-C₆H₄[C(O)N(H)(CH₂)₃N⁺(CH₃)₃]₂ | 2BF₄⁻ |
| 2.1b | see above | 2B(C₆H₅)₄⁻ |

-continued

| Compound | Cation | Anion |
|---|---|---|
| 3.1a | cis/trans H$_3$C—$^+$N(CH$_3$)(CH$_3$)(H$_2$C)$_3$N(H)—C(O)—[C$_6$H$_{10}$]—C(O)—N(H)(CH$_2$)$_3$N$^+$(CH$_3$)(CH$_3$)—CH$_3$ | 2BF$_4^-$ |
| 3.1b | see above | $2\text{B}[(\text{C}_6\text{H}_6)_4]^-$ |
| 3.1c | see above | $2\text{B}[(\text{C}_6\text{H}_5\text{–CH}_3)_4]^-$ |
| 3.1d | see above | $2\text{B}[(\text{C}_6\text{H}_5\text{–Cl})_6]^-$ |
| 3.1e | see above | $2\text{B}[(\text{naphthyl})_4]^-$ |
| 3.2a | cis/trans H—$^+$N(CH$_3$)(CH$_3$)(H$_2$C)$_3$N(H)—C(O)—[C$_6$H$_{10}$]—C(O)—N(H)(CH$_2$)$_3$N$^+$(CH$_3$)(CH$_3$)—H | 2BF$_4^-$ |
| 3.2b | see above | $2\text{B}[(\text{C}_6\text{H}_6)_4]^-$ |
| 3.2c | see above | $2\text{B}[(\text{C}_6\text{H}_5\text{–CH}_3)_4]^-$ |
| 3.2d | see above | $2\text{B}[(\text{C}_6\text{H}_5\text{–Cl})_4]^-$ |
| 3.2e | see above | $2\text{B}[(\text{naphthyl})_4]^-$ |
| 3.3a | cis/trans H$_5$C$_2$—$^+$N(C$_2$H$_5$)(C$_2$H$_5$)(H$_2$C)$_3$N(H)—C(O)—[C$_6$H$_{10}$]—C(O)—N(H)(CH$_2$)$_3$N$^+$(C$_2$H$_5$)(C$_2$H$_5$)—C$_2$H$_5$ | 2BF$_4^-$ |

-continued

| Compound | Cation | Anion |
|---|---|---|
| 3.3b | see above | $2B\left[\bigcirc\right]_4^-$ |
| 3.4a | $H_3C-\overset{CH_3}{\underset{CH_3}{\overset{|}{N}}}-(H_2C)_2N\overset{H}{\underset{}{-}}\overset{O}{\underset{}{C}}-[H]-\overset{O}{\underset{}{C}}-\overset{H}{\underset{}{N}}(CH_2)_2\overset{CH_3}{\underset{CH_3}{\overset{|}{N}^+}}-CH_3$ | $2BF_4^-$ |
| 3.4b | see above | $2B\left[\bigcirc\right]_4^-$ |
| 3.5a | $H_3C-\overset{CH_3}{\underset{CH_3}{\overset{|}{+N}}}(H_2C)_{10}N\overset{H}{\underset{}{-}}\overset{O}{\underset{}{C}}-[H]-\overset{O}{\underset{}{C}}-\overset{H}{\underset{}{N}}(CH_2)_{10}\overset{CH_3}{\underset{CH_3}{\overset{|}{N}^+}}-CH_3$ | $2BF_4^-$ |
| 3.5b | see above | $2B\left[\bigcirc\right]_4^-$ |
| 4.1a | (cyclohexane-1,3-bis(amide) structure with two $-(CH_2)_3N^+(CH_3)_3$ groups) | $2BF_4^-$ |
| 4.1b | see above | $2B\left[\bigcirc\right]_4^-$ |
| 5.1a | $H_3C-\overset{CH_3}{\underset{CH_3}{\overset{|}{+N}}}(H_2C)_3N\overset{H}{\underset{}{-}}\overset{O}{\underset{}{C}}-\overset{O}{\underset{}{C}}-\overset{H}{\underset{}{N}}(CH_2)_3\overset{CH_3}{\underset{CH_3}{\overset{|}{N}^+}}-CH_3$ | $2BF_4^-$ |
| 5.1b | see above | $2B\left[\bigcirc\right]_4^-$ |
| 6.1a | $H_3C-\overset{CH_3}{\underset{CH_3}{\overset{|}{+N}}}(H_2C)_3N\overset{H}{\underset{}{-}}\overset{O}{\underset{}{C}}(CH_2)_2\overset{O}{\underset{}{C}}-\overset{H}{\underset{}{N}}(CH_2)_3\overset{CH_3}{\underset{CH_3}{\overset{|}{N}^+}}-CH_3$ | $2BF_4^-$ |
| 6.1b | see above | $2B\left[\bigcirc\right]_4^-$ |
| 6.1c | see above | $2B\left[\bigcirc-CH_3\right]_4^-$ |

| Compound | Cation | Anion |
|---|---|---|
| 6.1d | see above | $2B\left[\bigcirc\!-\!Cl\right]_4^-$ |
| 6.1e | see above | $2B\left[\bigcirc\!\bigcirc\right]_4^-$ |
| 6.2a | H—⁺N(CH₃)(CH₃)(H₂C)₃N(H)—C(=O)(CH₂)₂C(=O)—N(H)(CH₂)₃N⁺(CH₃)(CH₃)—H | $2BF_4^-$ |
| 6.2b | see above | $2B\left[\bigcirc\right]_4^-$ |
| 6.2c | see above | $2B\left[\bigcirc\!-\!CH_3\right]_4^-$ |
| 6.2d | see above | $2B\left[\bigcirc\!-\!Cl\right]_4^-$ |
| 6.2e | see above | $2B\left[\bigcirc\!\bigcirc\right]_4^-$ |
| 6.3a | H₅C₂—⁺N(CH₃)(CH₃)(H₂C)₃N(H)—C(=O)(CH₂)₂C(=O)—N(H)(CH₂)₃N⁺(CH₃)(CH₃)—C₂H₅ | $2BF_4^-$ |
| 6.3b | see above | $2B\left[\bigcirc\right]_4^-$ |
| 6.4a | H₃C—⁺N(C₂H₅)(C₂H₅)(H₂C)₃N(H)—C(=O)(CH₂)₂C(=O)—N(H)(CH₂)₃N⁺(C₂H₅)(C₂H₅)—CH₃ | $2BF_4^-$ |
| 6.4b | see above | $2B\left[\bigcirc\right]_4^-$ |

-continued

| Compound | Cation | Anion |
|---|---|---|
| 6.4c | see above | $2B\left[\bigcirc\!\!-\!CH_3\right]_4^-$ |
| 6.4d | see above | $2B\left[\bigcirc\!\!-\!Cl\right]_4^-$ |
| 6.4e | see above | $2B\left[\text{naphthyl}\right]_4^-$ |
| 6.5a | $H_5C_2\!-\!\overset{C_2H_5}{\underset{C_2H_5}{+\!N}}\!(H_2C)_3\overset{H}{N}\!-\!\overset{O}{\overset{\|}{C}}(CH_2)_2\overset{O}{\overset{\|}{C}}\!-\!\overset{H}{N}(CH_2)_3\overset{C_2H_5}{\underset{C_2H_5}{N^+}}\!-\!C_2H_5$ | $2BF_4^-$ |
| 6.5b | see above | $2B\left[\bigcirc\right]_4^-$ |
| 7.1a | $H_3C\!-\!\overset{CH_3}{\underset{CH_3}{+\!N}}(H_2C)_3\overset{H}{N}\!-\!\overset{O}{\overset{\|}{C}}(CH_2)_4\overset{O}{\overset{\|}{C}}\!-\!\overset{H}{N}(CH_2)_3\overset{CH_3}{\underset{CH_3}{N^+}}\!-\!CH_3$ | $2BF_4^-$ |
| 7.1b | see above | $2B\left[\bigcirc\right]_4^-$ |
| 8.1a | $H_3C\!-\!\overset{CH_3}{\underset{CH_3}{+\!N}}(H_2C)_3\overset{H}{N}\!-\!\overset{O}{\overset{\|}{C}}(CH_2)_6\overset{O}{\overset{\|}{C}}\!-\!\overset{H}{N}(CH_2)_3\overset{CH_3}{\underset{CH_3}{N^+}}\!-\!CH_3$ | $2BF_4^-$ |
| 8.1b | see above | $2B\left[\bigcirc\right]_4^-$ |
| 9.1a | $H_3C\!-\!\overset{CH_3}{\underset{CH_3}{+\!N}}(H_2C)_3\overset{H}{N}\!-\!\overset{O}{\overset{\|}{C}}\!-\!\overset{CH_2}{\overset{\|}{}}\!-\!CH_2\!-\!\overset{O}{\overset{\|}{C}}\!-\!\overset{H}{N}(CH_2)_3\overset{CH_3}{\underset{CH_3}{N^+}}\!-\!CH_3$ | $2BF_4^-$ |
| 9.1b | see above | $2B\left[\bigcirc\right]_4^-$ |
| 10.1a | $H_3C\!-\!\overset{CH_3}{\underset{CH_3}{+\!N}}(H_2C)_3\overset{H}{N}\!-\!\overset{O}{\overset{\|}{C}}\!-\!H_2C\!-\!O\!-\!CH_2\!-\!CH_2\!-\!O\!-\!CH_2\!-\!\overset{O}{\overset{\|}{C}}\!-\!\overset{H}{N}(CH_2)_3\overset{CH_3}{\underset{CH_3}{N^+}}\!-\!CH_3$ | $2BF_4^-$ |

| Compound | Cation | Anion |
|---|---|---|
| 10.1b | see above | $2B\left[\bigcirc\right]_4^-$ |
| 11.1a | $H_3C-\overset{CH_3}{\underset{CH_3}{\overset{+}{N}}}(H_2C)_3N\underset{O}{\overset{O}{\diagdown}}\bigcirc\underset{O}{\overset{O}{\diagdown}}N(CH_2)_3-\overset{CH_3}{\underset{CH_3}{\overset{+}{N}}}-CH_3$ | $2BF_4^-$ |
| 11.1b | see above | $2B\left[\bigcirc\right]_4^-$ |
| 11.1c | see above | $2B\left[\bigcirc-CH_3\right]_4^-$ |
| 11.1d | see above | $2B\left[\bigcirc-Cl\right]_4^-$ |
| 11.1e | see above | $2B\left[\bigcirc\bigcirc\right]_4^-$ |
| 11.2a | $H-\overset{CH_3}{\underset{CH_3}{\overset{+}{N}}}(H_2C)_3N\underset{O}{\overset{O}{\diagdown}}\bigcirc\underset{O}{\overset{O}{\diagdown}}N(CH_2)_3-\overset{CH_3}{\underset{CH_3}{\overset{+}{N}}}-H$ | $2BF_4^-$ |
| 11.2b | see above | $2B\left[\bigcirc\right]_4^-$ |
| 12.1a | $H_3C-\overset{CH_3}{\underset{CH_3}{\overset{+}{N}}}(H_2C)_3\overset{H}{N}-\overset{O}{\overset{\|}{C}}\bigcirc\underset{O}{\overset{O}{\diagdown}}N(CH_2)_3\overset{+}{N}\overset{CH_3}{\underset{CH_3}{-CH_3}}$ | $2BF_4^-$ |
| 12.1b | see above | $2B\left[\bigcirc\right]_4^-$ |

-continued

| Compound | Cation | Anion |
|---|---|---|
| 13.1a | [structure: naphthalene diimide with two -N(CH₂)₃N⁺(CH₃)₃ groups] | 2BF₄⁻ |
| 13.1b | see above | 2B(C₆H₅)₄⁻ |
| 13.1c | see above | 2B(C₆H₄CH₃)₄⁻ |
| 13.1d | [structure: naphthalene diimide with two -N(CH₂)₃N⁺(CH₃)₃ groups] | 2B(C₆H₄Cl)₄⁻ |
| 13.1e | see above | 2B(naphthyl)₄⁻ |
| 13.2a | [structure: naphthalene diimide with two imidazolium-methyl-(CH₂)₃N groups] | 2BF₄⁻ |
| 13.2b | see above | 2B(C₆H₅)₄⁻ |
| 13.3a | [structure: naphthalene diimide bis(phenyl-carboxamido-propyl-trimethylammonium)] | 2BF₄⁻ |
| 13.3b | see above | 2B(C₆H₅)₄⁻ |

| Compound | Cation | Anion |
|---|---|---|
| 14.1a | H₃C—⁺N(CH₃)(CH₃)(H₂C)₃N(H)—C(O)—H₂C—C(OH)(COOH)—CH₂—C(O)—N(H)(CH₂)₃—⁺N(CH₃)(CH₃)—CH₃ | $2BF_4^-$ |
| 14.1b | see above | $2B[(C_6H_5)]_4^-$ |
| 15.1a | H₃C—⁺N(CH₃)(CH₃)(H₂C)₃N—[C(O)—H₂C / C(O)—H₂C]N(CH₂)₂N[CH₂—C(O) / CH₂—C(O)]—N(CH₂)₃⁺N(CH₃)(CH₃)—CH₃ | $2BF_4^-$ |
| 15.1b | see above | $2B[(C_6H_5)]_4^-$ |
| 16.1a | H₃C—⁺N(CH₃)(CH₃)(H₂C)₃N(CH₃)—C(O)—C₆H₄—C(O)—N(CH₃)(CH₂)₃—⁺N(CH₃)(CH₃)—CH₃ | $2BF_4^-$ |
| 16.1b | see above | $2B[(C_6H_5)]_4^-$ |
| 17.1a | (H₃C)(H₃C)⁺N-piperazine-N—C(O)—C₆H₄—C(O)—N-piperazine-N⁺(CH₃)(CH₃) | $2BF_4^-$ |
| 17.1b | see above | $2B[(C_6H_5)]_4^-$ |

The biscationic acid amide and imide derivatives and mixtures and mixed crystals thereof with mixed anions and/or cations, of the abovementioned general formulae (I) to (III), can be prepared by reaction of the acid amide or imide derivatives of the general formulae (IV) to (VI)

$$R_2-\overset{R_1}{\underset{R_3}{K^+}}-A-\overset{R_7}{N}-\underset{O}{\overset{}{C}}-W^1-\underset{O}{\overset{}{C}}-\overset{R_8}{N}-A'-\overset{R_4}{\underset{R_6}{K'^+}}-R_5 \quad 2X^-, \quad (IV)$$

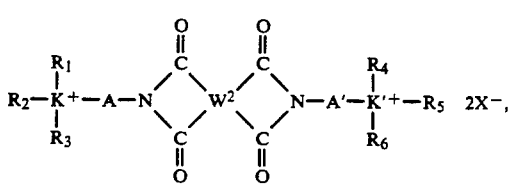

(V)

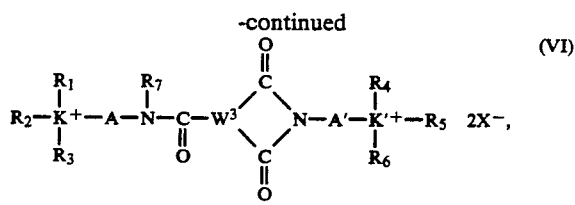

(VI)

in which $R_1$ to $R_8$, A and A', K and K' and $W^1$, $W^2$ and $W^3$ have the abovementioned meanings and $X^{-1}$ is the stoichiometric equivalent of one or more halogen anion(s), for example chlorine, bromine or iodine anion(s), or acetate, methyl-sulfate, ethyl-sulfate, hydrogen sulfate or sulfate anion(s), with a borate salt in water or mixtures of water and acid, such as, for example, acetic acid, or mixtures of water and organic solvent, such as, for example, isopropanol, isobutanol or methyl isobutyl ketone, at temperatures from about 10° C. to about 90° C., preferably from about 20° C. to about 40° C. The compounds, compound mixtures or mixed crystals of the abovementioned general formulae (I) to (III) are obtained in a good yield and purity in this reaction and can be isolated directly from the reaction medium by filtration.

The preparation of the compounds of the general formulae (IV) to (VI) is carried out in a manner which is known per se and is described in detail in the literature (for example Houben-Weyl, "Methoden der Organischen Chemie" (Methods of Organic Chemistry), Georg Thieme Verlag, 1985, Volume E 5, part 2, pages 924–1134 and loc. cit. 1958, Volume 11/2, pages 591–630).

The compounds (IV) are thus prepared, for example, by reaction of the aliphatic, cycloaliphatic, araliphatic or iso- or heterocyclic aromatic dicarboxylic acids or suitable dicarboxylic acid derivatives, such as, for example, esters, amides, acid chlorides or acid anhydrides thereof, with amines or amino compounds which contain at least one tertiary and at least one primary or secondary amino group in an inert reaction medium or in excess amine as the reaction medium, and subsequent bisprotonation with an inorganic or organic acid or bisquaternization with a suitable quaternizing reagent. The use of dicarboxylic acid dihalides or of dicarboxylic acid diesters as starting substances is preferred for the preparation of the compounds /IV]. A particularly preferred preparation process is the aminolysis of dicarboxylic acid diesters, in particular the dimethyl or diethyl esters, with amines at elevated temperature, the alcohol formed being distilled off.

The compounds (V) are prepared, for example, by reaction of the aliphatic, cycloaliphatic, araliphatic or iso- or heterocyclic aromatic tetracarboxylic acids or suitable derivatives, such as, for example, esters, amides, acid chlorides or acid anhydrides thereof, in particular mono- or dianhydrides thereof, with amines or amino compounds which contain at least one tertiary and at least one primary amino group, and subsequent bisprotonation with an inorganic or organic acid or bisquaternization with a suitable quaternizing reagent. The reaction can be carried out either under acid catalysis in an aqueous medium or in aliphatic or aromatic carboxylic acids or in mixtures of water and such carboxylic acids. A particularly suitable carboxylic acid is acetic acid. However, the compounds (V) can also be prepared, if appropriate under acid catalysis, in optionally substituted, aliphatic or aromatic hydrocarbons at elevated temperature, the water formed being removed from the circulation. Toluene, xylene, chlorobenzene and o-dichlorobenzene may be mentioned as particularly suitable hydrocarbons. All the diimide-forming tetracarboxylic acids can in principle be used as the tetracarboxylic acids. Aromatic tetracarboxylic acids in which in each case two carboxylic acid groups are in the ortho- or peri-position relative to one another are preferred.

The compounds (VI) are prepared by suitable combination of the processes described for compounds (IV) and (V).

All the suitable inorganic and organic acids or all the suitable alkylating agents are in principle possible for the bis-protonation or bis-quaternization. Particularly suitable acids are hydrochloric acid, sulfuric acid and acetic acid. Preferred alkylating agents are alkyl halides and dialkyl sulfates, in particular methyl chloride, methyl iodide and dimethyl and diethyl sulfate. Inert reaction media, such as, for example, dimethylformamide or aromatic hydrocarbons, are preferably possible as the reaction medium for carrying out the alkylation. However, anhydrous or water-containing alcohols, such as, for example, isobutanol or the isobutanol/water azeotrope having a water content of about 16% by weight, are also suitable. In individual cases, the quaternization can also be carried out in an aqueous medium.

The above compounds of the formulae 1.1a,b, 1.2a,b, 2.1.a,b, 3.1a,b, 4.1a,b, 6.1a,b, 6.2a,b, 11.1a,b, 11.2a,b, 12.1a,b, 13.1a,b and 17.1a,b are thus prepared, for example, by reaction of the following starting compounds 1.1, 1.2, 2.1., 3.1, 4.1, 6.1, 6.2, 11.1, 11.2, 12.1, 13.1 and 17.1

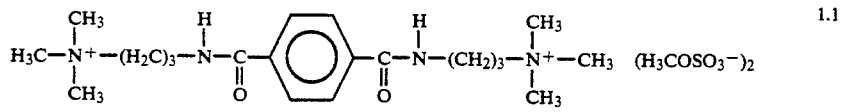

1.1

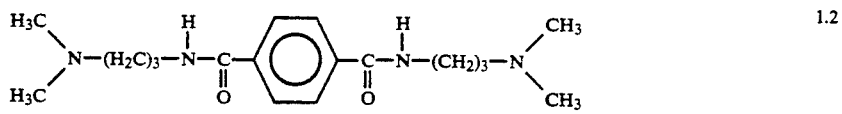

1.2

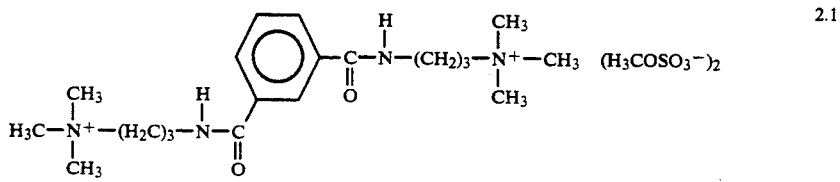

2.1

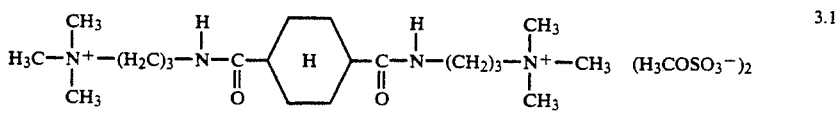

3.1 cis/trans

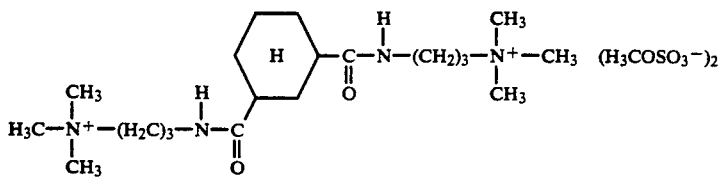

4.1 cis/trans

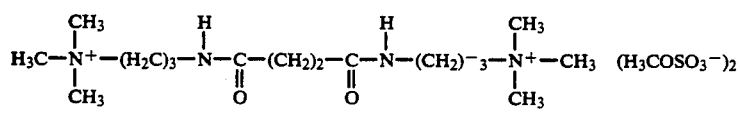

6.1

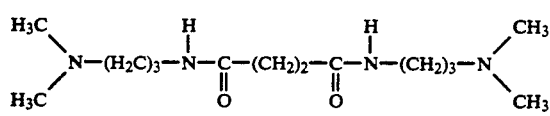

6.2

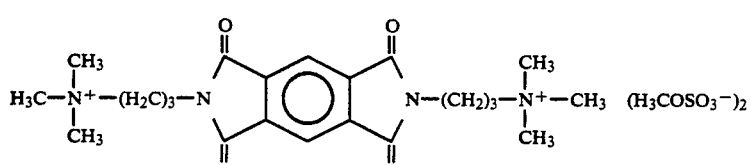

11.1

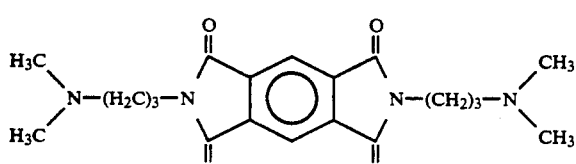

11.2

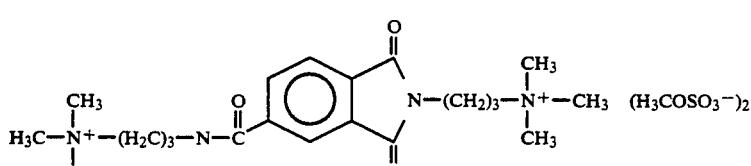

12.1

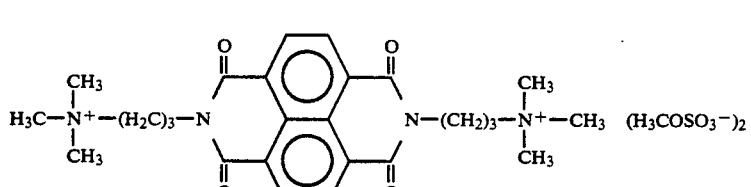

13.1

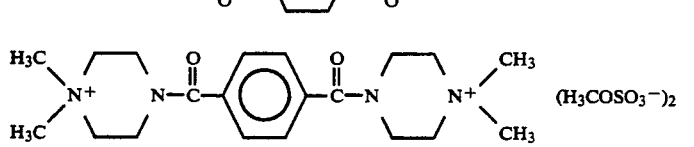

17.1 with sodium tetraphenylborate or sodium tetrafluoroborate (see following Preparation Examples 1 to 20).

The biscationic acid amide and imide derivatives according to the invention are outstandingly suitable for use as colorless charge control agents in toners and developers for electrophotographic recording processes and for use as charge-improving agents in powders and varnishes for surface coating, in particular in triboelectrically or electrokinetically sprayed powder varnishes.

The following preparation examples serve to illustrate the invention without limiting it thereto.

PREPARATION EXAMPLE 1

149.2 g (0.73 mol) of terephthaloyl dichloride are stirred into 3.5 l of anhydrous toluene, and 180.0 g (1.76 mol) of 3-dimethylamino-1-propylamine are then added dropwise at 20° to 30° C. in the course of 30 minutes, while cooling. The mixture is stirred at this temperature for 5 hours, subsequently heated for in each case 1 to 2 hours at 50° to 60° C. and 70° to 80° C. and then heated under reflux for 4 hours. The resulting product is filtered off with suction at 20° to 30° C., washed with toluene and dried at 100° C. in a vacuum cabinet. 292.4 g (0.72 mol) of the bisamide are obtained in the form of the bishydrochloride. The product is dissolved in 450 ml of water, and 180 g of 33% strength sodium hydroxide solution are added at 0° to 5° C. in the course of 30 minutes. The bisamide precipitates out in coarsely crystalline form during this operation. After the mixture has been stirred at 0° to 5° C. for one hour, the product is filtered off with suction, washed with 90 ml of ice-water and dried at 100° C. in a vacuum cabinet.

Yield: 221.2 g (90.7% of theory) of the compound 1.2, white powder

Molecular weight: 334

Melting point : 172°–174° C.

$^1$H—NMR (in DMSO-$d_6$): 1.65 (quintet, 4 methylene-H), 2.13 (singlet, 12 methyl-H), 2.28 (triplet, 4 methylene-H), 3.30 (quartet, 4 methylene-H), 7.90 (singlet, 4 phenylene-H), 8.63 (triplet, 2 amide-H) ppm.

PREPARATION EXAMPLE 2

66.8 g (0.2 mol) of the compound 1.2 are stirred into 1.6 l of toluene, and 100.8 g ( 0.8 mol ) of dimethyl sulfate are added at 20° to 30° C. in the course of 10 minutes. The mixture is stirred at 20° to 30° C. for 1 hour and then heated under reflux for 5 hours. After cooling to 20° to 30° C., the product is filtered off with suction, washed with toluene and dried at 100° C. in a vacuum cabinet.

Yield: 112.7 g (96.2% of theory) of the compound 1.1, white powder

Molecular weight: 586

Melting point: 180° C.

$^1$H—NMR (in $D_2O$): 2.18 (multipict, 4 methylene-H), 3.20 (singlet, 18 methyl-H), 3.50 (multiplet, 8 methylene-H), 3.75 (singlet, 6 methyl-H), 7.88 (singlet, 4 phenylene-H) ppm.

PREPARATION EXAMPLE 3

A solution of 13.7 g (40 mmol) of sodium tetraphenylborate in 50 ml of water is added dropwise to 100 ml of an aqueous solution of 10.0 g (17 mmol) of compound 1.1 at room temperature, while stirring. Compound 1.1b precipitates as a white precipitate during this operation. The precipitate is filtered off with suction, washed with water and dried in a circulating air cabinet at 60° C.

Yield: 17.0 g (99.8% of theory) of the compound 1.1 b, white powder

Molecular weight: 1002

Melting point: 255° C.

$^1$H—NMR (in DMSO—$d_6$): 1.98 (multiplet, 4 methylene-H), 3.03 (singlet, 18 methyl-H), 3.38 (multiplet, 8 methylene-H), 6.96 (multiplet, 40 phenyl-H), 7.95 (singlet, 4 phenylene-H), 8.64 (triplet, 2 amide-H) ppm.

PREPRATION EXAMPLE 4

The procedure is as in Preparation Example 3, with the difference that instead of sodium tetraphenylborate solution, a solution of 4.4 g (40 mmol) of sodium tetrafluoroborate in 50 ml of water is used and the reaction solution is concentrated to 30 ml and cooled to 2° C.

Yield: 8.9 g (97.3% of theory) of the compound 1.1a, white powder

Molecular weight: 538

Melting point: 228° C.

$^1$H—NMR (in DMSO-$d_6$): 1.99 (multipict, 4 methylene-H), 3.05 (singlet, 18 methyl-H), 3.38 (multiplet, 8 methylene-H), 7.93 (singlet, 4 phenylene-H), 8.62 (triplet, 2 amide-H) ppm.

PREPRATION EXAMPLE 5

5.0 g (15 mmol) of the compound 1.2 are suspended in 50 ml of water, and 2 N acetic acid are added until the pH reaches 7, the amine dissolving. A solution of 13.7 g (40 mmol) of sodium tetraphenylborate in 50 ml of water is then added dropwise, the product precipitating as a thick white precipitate. The reaction mixture is stirred at room temperature for 30 minutes and the precipitate is filtered off with suction, washed with water and dried at 60° C. in a circulating air cabinet.

Yield: 14.5 g (99.2% of theory) of the compound 1.2b, white powder

Molecular weight: 974

Melting point: 197° C.

$^1$H—NMR (in DMSO-de): 1.85 (multiplet, 4 methylene-H), 2.71 (singlet, 12 methyl-H), 3.00 (multiplet, 4 methylene-H), 3.35 (multiplet, 4 methylene-H), 6.96 (multiplet, 40 phenyl-H), 7.93 (singlet, 4 phenylene-H), 8.63 (triplet, 2 amide-H) ppm.

Preparation Example 6

109.5 g (0.75 mol) of dimethyl succinate are dissolved in 459 g (4.5 mol) of 3-dimethylamino-1-propylamine. The solution is then heated under reflux for 10 hours. Since the boiling point drops considerably due to the splitting off of methanol which quickly starts, it is ensured that the temperature in the gas phase remains above 125° C. by occasionally distilling off a methanol/amine mixture. Towards the end of the reaction time, the temperature in the gas phase is above 130° C. About 200 g of methanol/ amine mixture are distilled off in the course of the reaction. The mixture is then cooled to 20° to 30° C. and the reaction product which has crystallized out is filtered off with suction. Further product can be precipitated out of the liltrate by three-fold dilution with benzine. The product is washed free from amine with benzine and dried at 100° C. in a vacuum drying cabinet.

Yield: 188.0 g (87.6% of theory) of the compound 6.2, white powder

Molecular weight: 286

Melting point: 126°–128° C.

$^1$H—NMR (in DMSO-$d_6$): 1.48 (quintet, 4 methylene-H), 2.08 (singlet, 12 methyl-H), 2.20 (triplet, 4 methylene-H), 2.25 (singlet, 4 methylene-H), 3.05 (quartet, 4 methylene-H), 7.78 (triplet, 2 amide-H) ppm.

PREPARATION EXAMPLE 7

85.8 g (0.3 mol) of 6.2 are introduced into 610 ml of anhydrous dimethylformamide. A clear solution rapidly forms at room temperature. 189 g (1.5 mol) of dimethyl sulfate are then added dropwise at 30° to 40° C. in the course of about 15 minutes. A thick crystal sludge forms after a short time, which changes into a readily stirrable suspension on heating to 60° C. The suspension is subsequently stirred at 60° to 70° C. for 5 hours and, after cooling to 0° to 5° C., the product is filtered off with suction. It is washed thoroughly with toluene and dried in a vacuum cabinet at 100° C.

Yield: 151.0 g (93.6% of theory) of the compound 6.1, white powder

Molecular weight: 538

Melting point: 152° C.

$^1$H—NMR (in DMSO-$d_6$): 1.85 (multiplet, 4 methylene-H), 2.33 (singlet, 4 methylene-H), 3.05 (singlet, 18 methyl-H), 3.20 (multiplet, 8 methylene-H), 3.40 (singlet, 6 methyl-H), 7.95 (triplet, 2 amide-H) ppm.

PREPARATION EXAMPLE 8

The procedure is as in Preparation Example 3, with the difference that instead of the compound 1.1, 10.0 g (18.5 mmol) of the compound 6.1 are used.

Yield: 17.3 g (98.0% of theory) of the compound 6.1 b, white powder
Molecular weight: 954
Melting point: 245° C.
$^1$H—NMR (in DMSO-$d_6$): 1.81 (multiplet, 4 methylene-H), 2.37 (singlet, 4 methylene-H), 3.02 (singlet, 18 methyl-H), 3.12 (quartet, 4 methylene-H), 3.24 (multiplet, 4 methylene-H), 6.97 (multiplet, 40 phenyl-H), 7.90 (triplet, 2 amide-H) ppm.

PREPRATION EXAMPLE 9

The procedure is as in Preparation Example 5, with the difference that instead of the compound 1.2., 5.0 g (17.5 mmol) of the compound 6.2 are used.

Yield: 15.7 g (96.9% of theory) of the compound 6.2 b, white powder
Molecular weight: 926
Melting point: 183° C.
$^1$H—NMR (in DMSO-$d_6$): 1.72 (multiplet, 4 methylene-H), 2.38 (singlet, 4 methylene-H), 2.68 (singlet, 12 methyl-H), 2.95 (multiplet, 4 methylene-H), 3.12 (quartet, 4 methylene-H), 7.01 (multiplet, 40 phenyl-H), 7.92 (triplet, 2 amide-H) ppm.

PREPARATION EXAMPLE 10

18.0 g (1.0 mol) of pyromellitic acid dianhydride are stirred into 1.2 l of glacial acetic acid, and 306 g (3.0 mol) of 3-dimethylamino-1-propylamine are added dropwise at 40° to 50° C., while cooling. The mixture is then heated under reflux for 3 hours, 920 ml of o-dichlorobenzene are added and most of the glacial acetic acid is distilled off. The mixture is then heated, while passing over a stream of nitrogen and distilling off the residual glacial acetic acid, until the boiling point of o-dichlorobenzene is reached and heating is continued under reflux for 6 hours. After the mixture has been cooled to 20° to 30° C. the product which has precipitated out is filtered off with suction, washed with benzine and dried at 100° C. in a vacuum cabinet.

Yield: 271.0 g (70.2% of theory) of the compound 11.2, white powder
Molecular weight: 386
Melting point: 186°–188° C.
$^1$H—NMR (in DMSO-$d_6$): 1.75 (quintet, 4 methylene-H), 2.08 (singlet, 12 methyl-H), 2.25 (triplet, 4 methylene-H), 3.68 (triplet, 4 methylene-H), 8.15 (singlet, 2 phenylene-H) ppm.

PREPARATION EXAMPLE 11

7.2 g (0.2 mol) of the compound 11.2 are stirred in 600 ml of dimethylformamide, and 126.0 g (1.0 mol) of dimethyl sulfate are added dropwise at 30° to 40° C. in the course of 20 minutes, while cooling. The mixture is heated at 130° to 135° C. for 5 hours and, after cooling to 20° to 30° C. the product is filtered off with suction The product is washed with toluene and dried at 100° C. in a vacuum cabinet.

Yield: 121.9 g (95.5% of theory) of the compound 11.1, white powder
Molecular weight: 638
Melting point: 299° C.
$^1$H—NMR (in $D_2O$ ): 2.23 (multiplet, 4 methylene-H), 3.15 (singlet, 18 methyl-H), 3.48 (multiplet, 4 methylene-H), 3.73 (singlet, 6 methyl-H), 3.88 (triplet, 4 methylene-H), 8.33 (singlet, 2 phenylene-H) ppm.

PREPARATION EXAMPLE 12

The procedure is as in Preparation Example 4, with the difference that instead of the compound 1.1, 10.0 g (16 mmol) of compound 11.1 are used and the mixture is neither concentrated nor cooled.

Yield: 8.4 g (89.0% of theory) of the compound 11.1a, white powder
Molecular weight: 590
Melting point: >3 00° C.
$^1$H—NMR (in DMSO-$d_6$): 2.1 2 (multiplet, 4 methylene-H), 3.0 5 (singlet, 18 methyl-H), 3.35 (multiplet, 4 methylene-H), 3.71 (triplet, 4 methylene-H), 8.26 (singlet, 2 phenylene-H) ppm.

PREPARATION EXAMPLE 13

The procedure is as in Preparation Example 12, with the difference that instead of sodium tetrafluoroborate solution, a solution of 13.7 g (40 mmol) of sodium tetraphenylborate in 50 ml of water is used.

Yield: 16.8 g (99.6% of theory) of the compound 11.1b, pale yellow powder
Molecular weight: 1054
Melting point: 295° C.
$^1$H—NMR (in DMSO-$d_6$): 2.08 (multiplet, 4 methylene-H), 2.97 (singlet, 18 methyl-H), 3.36 (multiplet, 4 methylene-H), 3.70 (triplet, 4 methylene-H), 6.98 (multiplet, 40 phenyl-H), 8.28 (singlet, 2 phenylene-H) ppm.

PREPARATION EXAMPLE 14

1.5 g (0.25 mol) of naphthalene-1,4,5,8-tetracarboxylic acid 1,8-monoanhydride are stirred into 500 ml of glacial acetic acid, and 93.8 g (0.75 mol) of N-(3-aminopropyl)imidazole are added dropwise at 40° to 50° C., while cooling gently. The mixture is then heated under reflux for 6 hours. The resulting solution of the reaction product is poured into 2.5 l of water, and 1.01 kg of 33% strength sodium hydroxide solution are then added dropwise at 20° to 30° C., while cooling, whereupon the product precipitates out. It is filtered off with suction, washed thoroughly with water and dried at 100° C. in a vacuum cabinet.

Yield: 116.4 g (96.6% of theory) of the compound 13.4, white powder
Molecular weight: 482
Melting point: 260°–263° C.

PREPARATION EXAMPLE 15

6.4 g (0.2 mol) of the compound 13.4 are stirred into 600 ml of dimethylformamide, and 189.0 g (1.5 mol) of dimethyl sulfate are added dropwise at 30° to 40° C. in the course of 10 minutes, while cooling gently. The mixture is then stirred at 130° to 135° C. for 5 hours. After cooling to 20° to 30° C., the product is filtered off with suction, washed with 100 ml of dimethylformamide and then with toluene and dried at 100° C. in a vacuum cabinet.

Yield: 141.8 g (96.6% of theory) of the compound 13.2, pale yellow powder
Molecular weight: 734
Melting point: 261° C.
$^1$H—NMR (in $D_2O$) 2.35 (quintet, 4 methylene-H), 3.68 (singlet, 6 methyl-H), 3.95 (singlet, 6 methyl-H), 4.10 (triplet, 4 methylene-H), 4.39 (triplet, 4 methylene-H), 7.60 (multiplet, 4 imidazoyl-H), 8.40 (singlet, 4 naphthylene-H), 8.86 (singlet, 2 imidazoyl-H) ppm.

PREPARATION EXAMPLE 16

The procedure is as in Preparation Example 4, with the difference that instead of compound 1.1, 10.0 g (15 mmol) of the compound 13.1 are used and the mixture is neither concentrated nor cooled.

Yield: 9.3 g (96.9% of theory of the compound 13.1 a, pale yellow powder
Molecular weight: 640
Melting point: >300° C. (decomposition)
$^1$H—NMR (in DMSO-$d_6$): 2.20 (multiplet, 4 methylene-H), 3.05 (singlet, 18 methyl-H), 3.46 (multiplet, 4 methylene-H), 4.19 (triplet, 4 methylene-H), 8.68 (singlet, 4 naphthylene-H) ppm.

PREPARATION EXAMPLE 17

The procedure is as in Preparation Example 16, with the difference that instead of sodium tetrafluoroborate solution, a solution of 13.7 g (40 mmol) of sodium tetraphenylborate in 50 ml of water is used.

Yield: 14.0 g (84.5% of theory) of the compound 13.1 b, yellow powder
Molecular weight: 1104
Melting point: 287° C. (decomposition)
$^1$H—NMR (in DMSO-$d_6$): 2.13 (multiplet, 4 methylene-H), 3.00 (singlet, 18 methyl-H), 3.45 (multiplet, 4 methylene-H), 4.16 (triplet, 4 methylene-H), 6.90 (multiplet, 40 phenyl-H), 8.71 (singlet, 4 naphthylene-H) ppm.

PREPRATION EXAMPLE 18

The procedure is as in Preparation Example 3, with the difference that instead of the compound 1.1, 10.0 g (17 mmol) of the compound 3.1 are used.

Yield: 7.8 g (45.5% of theory) of the compound 3.1b, white powder
Molecular weight: 1008
Melting point: 255° C.
$^1$H—NMR (in DMSO-$d_6$): 1.35 (multiplet, 4 methylene-H), 1.79 (multiplet, 8 cyclohexylene-H), 2.08 (multiplet, 2 cycohexylene-H (sic)), 3.01 (singlet, 18 methyl-H), 3.09 (multiplet, 4 methylene-H), 3.25 (multiplet, 4 methylene-H), 7.00 (multiplet, 40 phenyl-H), 7.81 (triplet, 2 amide-H) ppm.

PREPARATION EXAMPLE 19

1.5 g (0.5 mol) of terephthaloyl dichloride are dissolved in 2.3 l of toluene, and 120 g (1.2 mol) of N-methylpiperazine are added dropwise at 20° to 30° C., while cooling. The mixture is stirred at 20° to 30° C. for 1 hour, subsequently heated to the reflux temperature in the course of 2 hours and boiled under reflux for 4 hours. After cooling to room temperature, the product is filtered off with suction, washed with toluene and dried. The dry product is dissolved in 400 ml of water, the solution is clarified with active charcoal and kieselguhr and the bisamide is precipitated by addition of 33% strength NaOH at 0° to 5° C. The bisamide is filtered off with suction, washed with water and dried at 100° C. in vacuo. 66 g (0.2 mol) of the dry bisamide are dissolved in 640 ml of dimethylformamide, and 76 ml (0.8 mol) of dimethyl sulfate are added dropwise in the course of 15 minutes at room temperature, while cooling gently. The mixture is then heated at 60° to 70° C. for 5 hours and the product is subsequently filtered off with suction at 0° to 5° C., washed with toluene and dried at 100° C. in vacuo.

Yield: 109 g (quantitative yield) of the compound 17,1, white powder
Molecular weight: 582
Melting point: >300° C.
$^1$H—NMR (in $D_2O$): 3.28 (singlet, 12 methyl-H), 3.53 (multiplet, 8 H piperazino-H), 3.73 (singlet, methyl-H of the methyl-sulfate anion, mostly hydrolyzed to hydrogen sulfate), 3.88 (multiplet, 4 piperazino-H), 4.13 (multiplet, 4 piperazion-H (sic)), 7.60 (singlet, 4 phenylene-H) ppm.

PREPARATION EXAMPLE 20

5.0 g (9 mmol) of the compound 17.1 are dissolved in 20 ml of water at room temperature. 2.2 g (20 mmol) of sodium tetrafluoroborate in 25 ml of water are then slowly added, the reaction mixture becoming very thick due to the crystals which precipitate out. The mixture is diluted with water to 250 ml and the colorless crystals are then filtered off with suction. After washing with water, the product is dried at 100° C. in a vacuum cabinet.

Yield: 3.8 g (79.1% of theory) of the compound 17.1a, white crystals
Molecular weight: 534
Melting point: >300° C.
$^1$H—NMR (in DMSO-$d_6$): 3.20 (singlet, 12 methyl-H), 3.48 (singlet, 8 piperazino-H), 3.83 (singlet, 8 piperazino-H), 7.56 (singlet, 4 phenylene-H) ppm.

PREPARATION EXAMPLE 21

The procedure is as in Preparation Example 20, with the difference that instead of sodium tetrafluoroborate, 7.0 g (20 mmol) of sodium tetraphenylborate, dissolved in 20 ml of water, are used.

Yield: 7.6 g (84.6% of theory) of the compound 17.1b, white powder
Molecular weight: 998
Melting point: 292° C. (decomposition)
$^1$H—NMR (in DMSO-$d_6$): 3.19 (singlet, 12 methyl-H), 3.46 (singlet, 8 piperazino-H), 3.82 (singlet, 8 piperazino-H), 7.03 (multiplet, 40 phenyl-H), 7.55 (singlet, 4 phenylene-H) ppm.

What is claimed is:

1. Biscationic acid amide or imide derivatives of the general formula I $$R_2-\overset{\overset{R_1}{|}}{\underset{\underset{R_3}{|}}{K^+}}-A-\overset{\overset{R_7}{|}}{N}-\overset{\overset{\|}{C}}{\underset{\|}{O}}-W^1-\overset{\overset{\|}{C}}{\underset{\|}{O}}-\overset{\overset{R_8}{|}}{N}-A'-\overset{\overset{R_4}{|}}{\underset{\underset{R_6}{|}}{K'^+}}-R_5 \qquad I$$

$$\left[R_{12}-\overset{\overset{R_9}{|}}{\underset{\underset{R_{11}}{|}}{B}}-R_{10}\right]_2^{\ominus}$$

in which $R_1$ to $R_8$ independently of one another are in each case a hydrogen atom or in each case a substituted or unsubstituted aliphatic group, which can be interrupted by hetero atoms, and in the case where $R_1$ and $R_2$, or $R_4$ or $R_5$ form a double bond to K or K', there is no $R_3$ or $R_6$ substituent, and in which A and A' and $W^1$ as a divalent bridge member independently of one another are in each case a substituted or unsubstituted aliphatic or aromatic bridge member which can be interrupted by hetero atoms, or $W^1$ is a direct bond, and K and K' are in each case a nitrogen atom, and the radicals $R_9$ to $R_{12}$ independently of one another are aliphatic, cycloaliphatic, aromatic or araliphatic radicals, in which the aliphatic, cycloaliphatic, aromatic and araliphatic radicals can be substituted by $C_1$–$C_4$-alkyl, $C_1$–$C_4$-alkoxy or aryl radicals, or halogen atoms, and mixtures of these compounds and mixed crystals with mixed anions and/or cations.

2. Biscationic acid amide derivative as claimed in claim 1 said derivative having the formula (Ia)

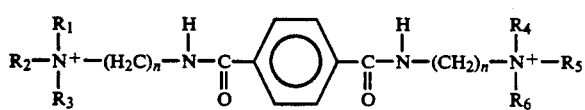

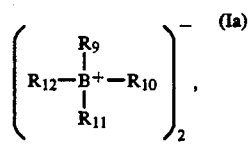

in which, independently of one another, $R_1$ and $R_4$ are H, $CH_3$ or $C_2H_5$, $R_2$, $R_3$, $R_5$ and $R_6$ are $CH_3$ or $C_2H_5$, n is 1 to 5 and $R_9$ through $R_{12}$ are all F or A phenyl.

3. Biscationic acid amide derivative as claimed in claim 1 said derivative having the formula (Ib)

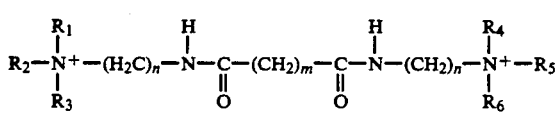

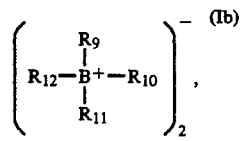

in which, independently of one another, $R_1$ and $R_4$ are H, $CH_3$ or $C_2H_5$, $R_2$, $R_3$, $R_5$ and $R_6$ are $CH_3$ or $CH_2$ or $C_2H_5$, m is 1 to 8, n is 2 or 3 and $R_9$ through $R_{12}$ are all F phenyl.

4. A process for the preparation of acid amide and imide derivatives or mixtures of acid amide and imide derivatives or mixed crystals with mixed anions or cations, or with anions and cations, of the general formula I as claimed in claim 1, comprising the step of reacting an acid amide or imide derivative of the general formula IV

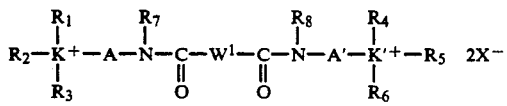

in which $R_1$ to $R_8$, A and A', K and K' and $W^1$ have the meanings given in claim 1 and X' is the stoichiometric equivalent of one or more halogen anions or methyl-sulfate, ethyl-sulfate, hydrogen sulfate or sulfate anion or anions, with one or more borate salts of the formula $Na^+(BR_9R_{10}R_{11}R_{12})^-$, where $R_9$ through $R_{12}$ are defined in claim 1, in water or mixtures of water and acid or mixtures of water and organic solvent at temperatures of greater than 10° C. and up to about 90° C.

5. A process as claimed in claim 4, wherein the compounds of the general formula (IV) are reacted in a mixture of water and acetic acid, isopropanol, isobutanol or methyl isobutyl ketone.

6. A process as claimed in claim 4, wherein the compounds of the general formula (IV) are reacted with sodium tetraphenylborate, sodium tetra-o-fluorophenylborate, sodium tetra-m-fluorophenylborate, sodium tetra-p-fluorophenylborate, sodium tetra-o-chlorophenylborate, sodium tetra-m-chlorophenylborate, sodium tetra-p-chlorophenylborate, sodium tetra-o-tolylborate, sodium tetra-m-tolylborate, sodium tetra-p-tolylborate, sodium tetra-1-naphthylborate, sodium tetra-2-naphthylborate, sodium tetra-o-methyoxyphenylborate, sodium tetra-m-methoxyphenylborate, sodium tetra-p-methoxyphenylborate, sodium tetra-o-biphenylborate, sodium tetra-m-biphenylborate, sodium tetra-p-biphenylborate, sodium tetrabenzylborate, sodium tetra-o-pyridylborate, sodium tetra-m-pyridylborate, sodium tetra-p-pyridylborate or sodium tetrafluoroborate.

* * * * *

UNITED STATES PATENT AND TRADEMARK OFFICE
CERTIFICATE OF CORRECTION

PATENT NO. : 5,329,046
DATED : July 12, 1994
INVENTOR(S) : Hans-Tobias Macholdt, et al It is certified that error appears in the above-indentified patent and that said Letters Patent is hereby corrected as shown below:

At column 1, line 7 "imdie" should read --imide--.

At column 1, line 33, "$R_2$" should read --$R_1$--.

At column 4, line 39 "-CHaC (COOH)-$CH_2$-" should read -- -CH=C(COOH)-$CH_2$- --.

At column 9, line 3 in the left portion of the formula 1.9a "$(H_2C)_2$" should read --$(H_2C)_3$--.

At column 21, line 3 and line 30 the formula for the cations of compounds 13.1a and 13.1d should read:

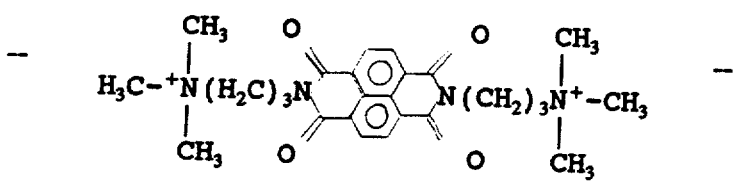

UNITED STATES PATENT AND TRADEMARK OFFICE
CERTIFICATE OF CORRECTION

PATENT NO. : 5,329,046
DATED : July 12, 1994
INVENTOR(S) : Hans-Tobias Macholdt, et al It is certified that error appears in the above-indentified patent and that said Letters Patent is hereby corrected as shown below:

column 29, line 32 "multipict" should read --multiplet--.

column 29, line 65 "multipict" should read --multiplet--.

column 30, line 16 "DMSO-de" should read --DMSO-$d_6$--.

column 30, line 36 "liltrate" should read --filtrate--.

column 32, line 33 "1.5g" should read --71.5g--.

column 32, line 51 "6.4g" should read --96.4g--.

column 33, line 46 "1.5g" should read --101.5g--.

column 33, line 68 "17,1" should read --17.1--.

claim 2, column 35, line 16 "A" should read --all--.

claim 2, column 35, line 15 in the formula Ia "$B^+$" should read --B--.

claim 3, column 35, line 26 in the formula Ib "$B^+$" should read --B--.

UNITED STATES PATENT AND TRADEMARK OFFICE
CERTIFICATE OF CORRECTION

PATENT NO. : 5,329,046
DATED : July 12, 1994
INVENTOR(S) : Hans-Tobias Macholdt, et al It is certified that error appears in the above-indentified patent and that said Letters Patent is hereby corrected as shown below:

claim 3, column 35, line 30, delete "or $CH_2$".

claim 3, column 35, line 32, insert --or all-- between "F" and "phenyl".

Signed and Sealed this

Twentieth Day of December, 1994

Attest:

BRUCE LEHMAN

*Attesting Officer*     *Commissioner of Patents and Trademarks*